United States Patent
Wang et al.

(10) Patent No.: US 12,259,543 B2
(45) Date of Patent: Mar. 25, 2025

(54) ULTRA-COMPACT FOLDED-BEAM PATH CONFOCAL ENDOMICROSCOPE

(71) Applicant: THE REGENTS OF THE UNIVERSITY OF MICHIGAN, Ann Arbor, MI (US)

(72) Inventors: Thomas D. Wang, Ann Arbor, MI (US); Haijun Li, Ann Arbor, MI (US); Xiyu Duan, San Jose, CA (US); Gaoming Li, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 505 days.

(21) Appl. No.: 17/439,725

(22) PCT Filed: Mar. 18, 2020

(86) PCT No.: PCT/US2020/023395
§ 371 (c)(1),
(2) Date: Sep. 15, 2021

(87) PCT Pub. No.: WO2020/191075
PCT Pub. Date: Sep. 24, 2020

(65) Prior Publication Data
US 2022/0155579 A1    May 19, 2022

Related U.S. Application Data

(60) Provisional application No. 62/820,023, filed on Mar. 18, 2019.

(51) Int. Cl.
G02B 23/24    (2006.01)
A61B 1/313    (2006.01)
G02B 21/00    (2006.01)

(52) U.S. Cl.
CPC .......... *G02B 23/2423* (2013.01); *A61B 1/313* (2013.01); *G02B 21/0028* (2013.01);
(Continued)

(58) Field of Classification Search
CPC ............ G02B 23/2423; G02B 21/0028; G02B 21/0048; G02B 21/0076; G02B 23/2469; A61B 1/313
(Continued)

(56) References Cited

U.S. PATENT DOCUMENTS

| 5,059,009 A | 10/1991 | McKinley |
| 6,172,789 B1 * | 1/2001 | Kino ................. G02B 21/0076 359/199.1 |

(Continued)

FOREIGN PATENT DOCUMENTS

| WO | WO-2018/102822 A1 | 6/2018 |
| WO | WO-2019/023287 A1 | 1/2019 |

OTHER PUBLICATIONS

Deliolanis et al., Performance of the red-shifted fluorescent proteins in deep-tissue molecular imaging applications, J. Biomed. Opt., 13(4):044008 (2008).

(Continued)

*Primary Examiner* — William Choi
(74) *Attorney, Agent, or Firm* — MARSHALL, GERSTEIN & BORUN LLP (57) ABSTRACT

A compact single-axis confocal endomicroscope is provided, capable of complying with 2.8 mm diameter endoscope space requirements. The single-axis confocal endomicroscope uses a folded path design achieved between a fixed mirror and a lateral plane scanning mirror thereby producing high numerical apertures that allow for diffraction-limited resolution in sub-surface scanning. The scan- (Continued)

ning mirror has a central aperture that allows for illumination beam expansion in the folded path design.

7 Claims, 6 Drawing Sheets

(52) U.S. Cl.
CPC ..... *G02B 21/0048* (2013.01); *G02B 21/0076* (2013.01); *G02B 23/2469* (2013.01)
(58) Field of Classification Search
USPC .......................................... 359/738
See application file for complete search history.

(56) References Cited

U.S. PATENT DOCUMENTS

| | | |
|---|---|---|
| 2002/0018276 A1 | 2/2002 | Suga |
| 2011/0211104 A1 | 9/2011 | Hendriks |
| 2012/0075685 A1 | 3/2012 | Hofmann et al. |
| 2016/0357008 A1 | 12/2016 | Li et al. |
| 2018/0356629 A1 | 12/2018 | Wang et al. |
| 2020/0000341 A1* | 1/2020 | Messerschmidt .. G02B 23/2469 |

OTHER PUBLICATIONS

Duan et al., MEMS-based multiphoton endomicroscope for repetitive imaging of mouse colon, Biomedical Optics Express, vol. 6, No. 8, 10 pp. (Aug. 2015).
Duan et al., Visualizing epithelial expression of EGFR in vivo with distal scanning side-viewing confocal endomicroscope, Sci. Rep., 6:37315 (2016).
Duan, MEMS-Based Confocal Endomicroscope for High Resolution Fluorescence Imaging, Dissertation, University of Michigan, 2017.
Hinoi et al., Mouse model of colonic adenoma-carcinoma progression based on somatic Apc inactivation, Cancer Res., 67(20):9721-30 (2007).
Hinoi et al., Silencing of CDX2 expression in colon cancer via a dominant repression pathway, J. Biol. Chem., 278(45):44608-16 (2003).
International Application No. PCT/US2020/023395, International Preliminary Report on Patentability, dated Sep. 16, 2021.
International Application No. PCT/US2020/023395, International Search Report and Written Opinion, mailed Jun. 3, 2020.
Kang et al., Endoscopic probe optics for spectrally encoded confocal microscopy, Biomed. Opt. Express, 4(10):1925-36 (2013).
Kim et al., In vivo wide-area cellular imaging by side-view endomicroscopy, Nat. Methods, 7(4):303-5 (2010).
Li et al., Integrated monolithic 3D MEMS scanner for switchable real time vertical/horizontal cross-sectional imaging, Opt. Express, 24(3):2145-55 (2016).
Li et al., Ultra-compact microsystems-based single axis confocal endomicroscope, IEEE Transactions on Medical Imaging, vol. 39, Issue 7, pp. 2406-2414 (Jul. 2020).
Lopez-Garcia et al., Intestinal stem cell replacement follows a pattern of neutral drift, Science, 330(6005):822-5 (2010).
Madisen et al., A robust and high-throughput Cre reporting and characterization system for the whole mouse brain, Nat. neurosci., 13(1):133-40 (2010).
Marten et al., Detection of dysplastic intestinal adenomas using enzyme-sensing molecular beacons in mice, Gastroenterology, 12292):406-14 (2002).
Rakic, Algorithm for the determination of intrinsic optical constants of metal films: application to aluminum, Appl. Opt., 34(22):4755-67 (1995).
Rowan et al., APC mutations in sporadic colorectal tumors: A mutational "hotspot" and interdependence of the "two hits", Proc. Natl. Acad. Sci. USA, 97(7):3352-7 (2000).
Skala et al., In vivo multiphoton microscopy of NADH and FAD redox states, fluorescence lifetimes, and cellular morphology in precancerous epithelia, Proc. Natl. Acad. Sci. USA, 104(49):19494-9 (2007).
Turner et al., Five parametric resonances in a microelectromechanical system, Nature, 396:149-52 (1998).
Wang et al., Functional imaging of colonic mucosa with a fibered confocal microscope for real-time in vivo pathology, Clin. Gastroenterol. Hepatol., 5(11):1300-5 (2007).
Wang et al., Gradient index lens based combined two-photon microscopy and optical coherence tomography, Opt. Express, 22(11):12962-70 (2014).
Zhou et al., EGFR Overexpressed in Colonic Neoplasia Can be Detected on Wide-Field Endoscopic Imaging, Clin. Transl. Gastroenterol., 6(7):e101 (2015).
Ducourthial et al., Development of a real-time flexible multiphoton microendoscope for label-free imaging in a live animal, Sci. Rep., Article No. 18303 (Dec. 2015).
European Patent Application No. 20774594, Extended European Search Report, mailed Nov. 4, 2022.
Shao et al., MEMS 3D scan mirror, Proceedings of SPIE, MOEMS Display and Imaging Systems II, 5348:175-83 (Jan. 2004).

\* cited by examiner

ULTRA-COMPACT FOLDED-BEAM PATH CONFOCAL ENDOMICROSCOPE

CROSS-REFERENCE TO RELATED APPLICATIONS

This application claims priority to U.S. Provisional Patent Application No. 62/820,023, filed Mar. 18, 2019, which is hereby incorporated by reference in its entirety.

FIELD OF THE DISCLOSURE

The present disclosure generally relates to techniques for imaging tissue using an optical instrument and, more particularly, to techniques using compact confocal endomicroscopes.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Many human diseases originate within the epithelium of hollow organs and ducts. This thin layer of tissue has dimensions of only a few hundred microns, a simple repetitive architecture, and intense self-renewal kinetics. Optical sectioning techniques have been developed to visualize molecular expression patterns within the epithelium. These techniques attempt to visualize, with sub-cellular resolution, unique biological processes that drive disease progression.

For in vivo imaging of the epithelium, optical scanning instruments must be sufficiently small in size and provide fast speed scanning. Confocal endomicroscopes have been developed for this purpose and are now being used routinely in the clinic. Confocal endomicroscopes use the core of a single mode optical fiber to act as "pinhole" rejecting light scattered from the epithelium tissue.

Unfortunately, current clinical endomicroscopes are limited in imaging performance by scanning mechanisms that are either too slow in speed resulting in motion artifacts, or too bulky in dimension requiring a fiber bundle that reduces resolution and flexibility and increases cost.

There is a desirability for a fast, compact scanner mechanism that can be placed in the distal end of the endomicroscope to provide improved performance and flexibility for instrument control.

SUMMARY

The present application describes single-axis confocal endomicroscopes, in a compact design, that may be used for imaging of tissue, in vivo. The techniques may be used to provide handheld optical devices for real-time tissue scanning, for "optical biopsy" and other applications.

We previously developed a miniature scanner to perform high speed in vivo imaging, with a design that uses parametric resonance where drive signals are applied at frequencies near $2\omega_o/n$ ($\omega_o$ is the natural frequency of vibrational modes and n is an integer $\geq 1$). These electrostatic devices were fabricated with compact dimensions using micro-electro-mechanical systems (MEMS) processes.

With the present techniques, MEMS-based confocal endomicroscope are now a reality having a compact design that, in some examples, achieves a much smaller outer diameter of 2.4 mm or below. That diameter makes it possible to have an endomicroscope that properly marries with the 2.8 mm biopsy channel of a standard medical endoscope.

The present techniques include a single flexible fiber configured to deliver and collect light using a folded beam path configuration that achieves a compacted design. The folded beam path configuration is achieved, in some examples, using a fast scanning assembly located in a distal probe end of the endomicroscope. That fast scanning assembly may be a scanning mirror positioned to facilitate a high numerical aperture in the endomicroscope. That facilitation occurs in part because of the folded beam path configuration of the scanning mirror and in particular because of the coordination of that folded beam path with exit surface of a single mode fiber without impediment from the scanning mirror.

In some examples, the scanning assembly includes two mirrors, one a fast scanning mirror and the other a fixed mirror, both positioned to fold both an incident (illumination beam path) and a reflected (detected beam path), through the endomicroscope. The scanning assembly further includes a compact lens assembly that has a high numerical aperture (NA) facilitated by these mirrors. By way of example, an NA of 0.4 or better and with a working distance of 50 µm and field-of-view of 250×250 µm² has been achieved.

In accordance with an example, an endomicroscope assembly comprises: a fiber ferrule and a single-mode optical fiber extending into the fiber ferrule, the fiber ferrule having a distal end positioned to emit an illumination beam when provided to the single-mode optical fiber; a compact scanning assembly mounted to the flexible tubing, the compact scanning assembly having a folded beam configuration to receive the illumination beam, to convert the illumination beam to a higher numerical aperture illumination beam, and to scan the higher numerical aperture illumination beam across a lateral sample region, the compact scanning assembly comprising: an outer housing; a dual mirror lateral scanning assembly fixedly positioned within the outer housing and adjacent the distal end of the flexible tubing, the dual mirror lateral scanning assembly having a first scanning mirror with an aperture aligned with the single mode fiber to receive the illumination beam into a folded beam path for converting to the higher numerical aperture illumination beam, the folded beam path being defined by the first scanning mirror and a second mirror; and a lens assembly fixedly positioned within the rigid outer housing, the lens assembly positioned distally to the lateral scanning assembly to scan the higher numerical aperture illumination beam across the lateral sample region and to collect fluorescence from the lateral sample region.

BRIEF DESCRIPTION OF THE DRAWINGS

For a more complete understanding of the disclosure, reference should be made to the following detailed description and accompanying drawing figures, in which like reference numerals identify like elements in the figures, and in which.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

A front-viewing confocal endomicroscope is provided having a fast, compact, distal scanner configured to collect real time in vivo optical sections. The confocal endomicroscope using a single optical fiber and a single axis folded beam path configuration design. To form that folded beam path, two having two mirrors, one a fixed mirror and the other a scanning mirror. Implemented by a two mirror MEMS assembly technology, the folded beam path configuration allows we were able to scale down the dimensions of the device for efficient packaging and perform rapid beam scanning. This capability provides significantly improved imaging performance in terms of speed and resolution compared with other endomicroscope designs currently used in the clinic. The present techniques show stable operation at fast frames rates (e.g., 20 frames per second and higher), with minimal interference from mechanical vibrations while imaging. In an example, using fluorescein staining, we were able to collect bright optical sections of in epithelium at a depth of ~50 µm. Further still, the present techniques provide for continuous image collection without any noticeable phase shifts at fixed drive frequencies. Position sensing with the device allows for further control of stabilizing operation in more versatile environments.

Figure 1:
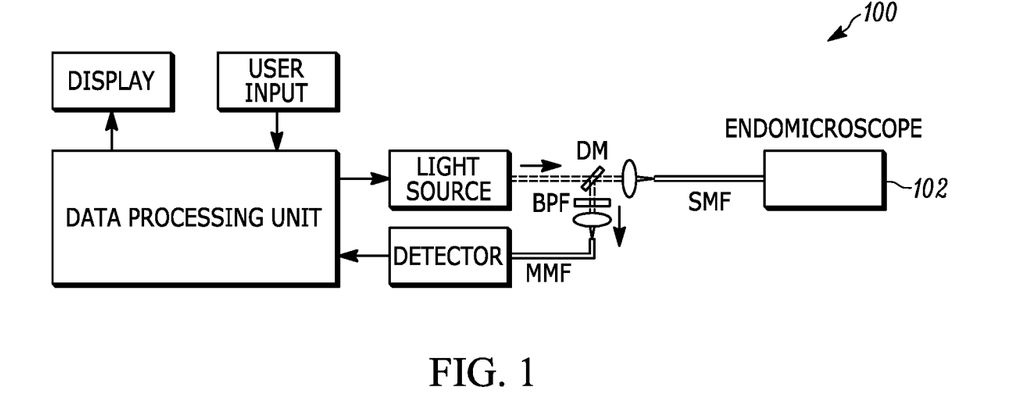
FIG. 1 illustrates a schematic of an imaging system having a single-axis confocal endomicroscope, in accordance with an example.

FIG. 1 illustrates a schematic 100 of an optical imaging system. The system 100 includes a single-axis confocal endomicroscope 102 for performing optical scanning on a sample. The optical scanning may be performed on an outer surface of a tissue sample. However, in examples detailed herein regarding FIG. 1, the endomicroscope scans at a sub-surface focal plane in the tissue, thereby allowing sub-surface in vivo scanning, including optical biopsy scanning.

In the illustrated example, the single-axis confocal endomicroscope 102 is coupled to a single mode fiber (SMF). The SMF is coupled to receive an illumination beam provided from a light source (e.g., a laser source) configured to provide that illumination beam via a dichroic mirror (DM) and a focusing element, lens L1, focusing the illumination beam into the SMF. The illumination beam may be focused by the endomicroscope to a focal plane subsurface in tissue, and that illumination beam may be scanned over that focal plane as described further.

The light source is controlled by a data processing unit, such as an image processor or other computer device(s). A display is coupled to the data processing unit, along with a user input device, such as a keyboard, keypad, touchpad, touchscreen, microphone, and/or other input devices.

Collected fluorescence reflected from the focal plane in the tissue is collected by the single-axis confocal endomicroscope 102 and provided to a detector, e.g., a photomultiplier, through the SMF and the first focusing element L1, the DM, and an optical band pass filter (BPF). Filtered collected fluorescence is coupled to a second focusing element, L2, which focuses the fluorescence into a multimode fiber (MMF). The collected fluorescence is received at the detector and digital output signals are provided to the data processing unit for analysis.

The data processing unit may analyze the collected fluorescence and processes the collected fluorescence beam to produce an output image provided to medical professions on the display. In some examples, the data processing unit may be part of a diagnostic system, where the data processing unit analyzes the collected fluorescence to identify pathologies and pathology locations in the image data, and thus in the sampled tissue region. In some examples, the image processing unit may be part of a treatment system, where the image processing unit develops a treatment response based on that identify pathology information.

The data processing unit may also control operation of the single-axis confocal endomicroscope 102. The data processing unit may be coupled to a digital to analog converter (DAC) (not shown) and may generate scanning control signals that are sent to the DAC, amplified, and used for driving two-dimensional (2D) scanning of the MEMS driver of the endomicroscope 102. For example, the MEMS driver may control scanning of the single-axis confocal endomicroscope 102 by controlling scanning of a scanning mirror, M1, discussed further below.

Figure 2:
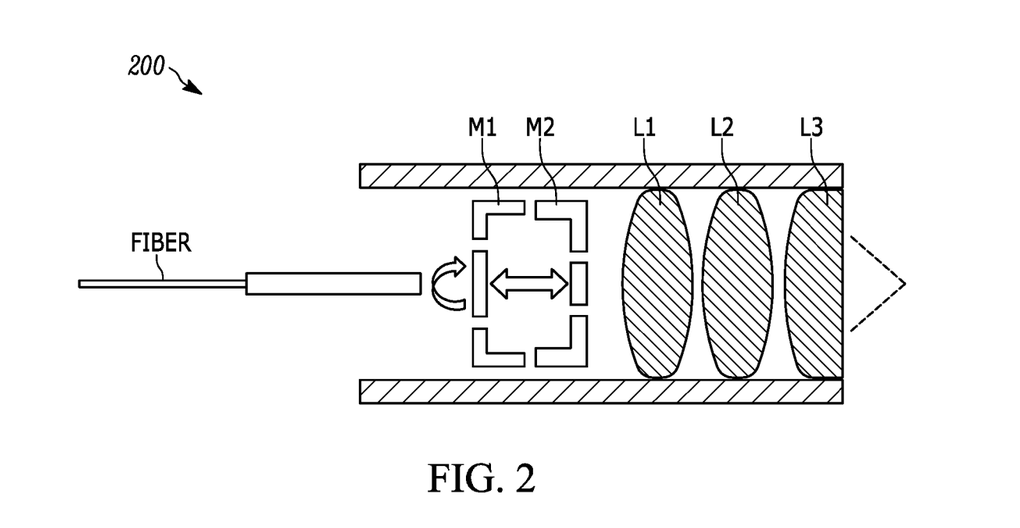
FIG. 2 illustrates a schematic design of the single-axis confocal endomicroscope of the imaging system of FIG. 1, in accordance with an example.

FIG. 2 illustrates a schematic design of a single-axis confocal endomicroscope 200, as may be used for the endomicroscope 102. An SMF feeds a distal end of the endomicroscope 200 which has a MEMS scanning assembly formed of two mirrors, M1 and M2, adjacent an exit surface of the SMF and configured to provide a folded beam path, that expands an illumination beam from the SMF before collimation by a lens assembly formed of lens elements, L1 and L2 and L$^3$, as shown. These lens elements are different than those described above in reference to FIG. 1. The mirror M1 is a scanning mirror, and the mirror M2 may be a fixed mirror or a scanning mirror. As such, the scanning mirror M1 is used to scan an illumination beam across a 2D sample region within a tissue, as well as to scan for a fluorescence captured beam across that 2D sample region. In the illustrated example, the mirror M2 may be used for static or out-of-plane scanning, thereby allowing for full 3D tissue region illumination and fluorescence capture scanning.

To develop the schematic design of FIG. 2, we performed ray-trace simulations to design the optic elements specifically for the 2.4 mm form factor confocal endomicroscope. The design criteria included diffraction-limited resolution on axis with working distance of 50 µm and field-of-view of 250×250 µm². Of course, other design criteria may be used for other size constraints on overall endomicroscope design.

In the illustrated schematic, the SMF-delivered illumination beam passes through an aperture of in the MEMS scanning mirror M1, impinges on the second scanning mirror M2 and is reflected by the second MEMS scanner M2 back into the actual scanning mirror surface of the mirror M1, which laterally scans the illumination beam in two-dimensions. Thus, the scanning assembly formed by mirrors M1 and M2 is an example lateral scanning assembly. Convergent lens L3 with high refractive index is used to increase the effective numerical aperture (NA), i.e., to a higher numerical aperture, and two achromatic doublet lens, L1 and L2, are used to correct aberration and dispersion.

Fluorescence is collected by the same optics and travels in the opposite direction along the same path, descanned by scanning mirror, M2, and focused into the same SMF. L2, L3, and L4 are designed to all have an outer diameters of at or about 2 mm for the desired endoscope outer diameter compatibility. In an implementation, the schematic design of FIG. 2 was used to produce an effective numerical aperture (NA) of 0.41 with a field-of-view (FOV) of 250×250 µm².

Figure 3:
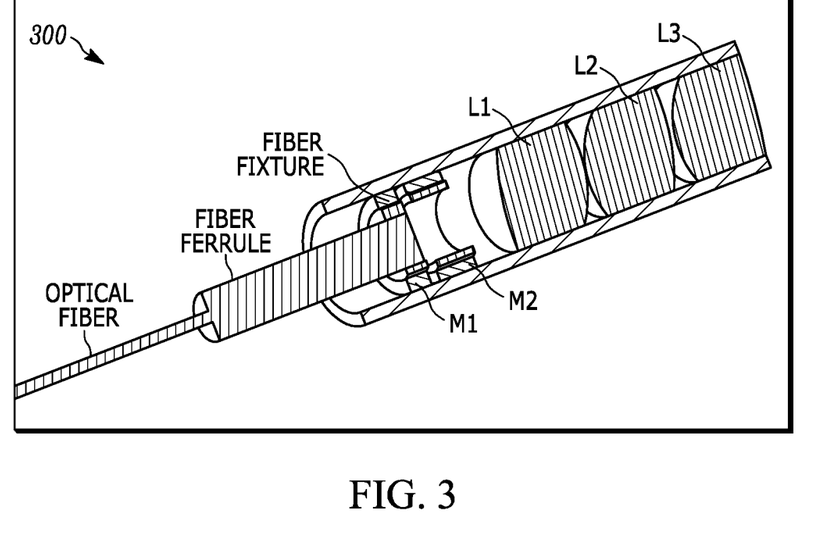
FIG. 3 is a cross-sectional view of the single-axis confocal endomicroscope of FIG. 2, in accordance with an example.

FIG. 3 illustrates a cross-sectional view of an assembled single-axis confocal endomicroscope 300 in accordance with an example of the schematic 200. An optical fiber (e.g., a SMF) is connected at a distal end to a fiber ferrule which engages a fiber fixture that retains the ferrule within a housing of the MEMS scanning assembly. Adjacent the end of the distal end of the fiber ferrule is the two mirror scanning assembly having 2D scanning mirror M1 and mirror M2, which may be a fixed mirror or a scanning mirror. The MEMS scanning assembly, like the fiber fixture, abuts the inner diameter of the housing and is retained in the housing against displacement. Lenses L1, L2, and L3 are positioned in the housing as well and retained in the housing by engagement of their outer diameter surfaces with the inner surface of the housing.

The scanning mirror M1 is a compact scanner designed and fabricated using MEMS processes. The mirror M1 has a reflector surface facing the mirror M2, and therefore facing away from the end of the exit surface of the fiber ferrule. The mirror M1 may be mounted on a gimbal frame to minimize vibrational cross-talk between orthogonal scanning axes (i.e., the X-axis and the Y-axis). The mirror may be rotated about either axis by drive signals applied to panels of electrostatic comb-drive actuators forming the scanning mirror M1. Inner and outer torsional springs may be designed to achieve resonant frequencies near 12 kHz and 3 kHz, for example. The reflective surface was formed using an Aluminum sputtered on the front-side silicon surface to achieve reflectivity >90% between 400 and 700 nm. Other reflectivity values over other frequencies ranges may be achieved as desired. Notably, the scanning mirror M1 and the reflective surface of the mirror M2 should be optimized for both the illumination beam and the collected fluorescence beam.

For in vivo imaging, we used driving frequencies of 24.64 and 6.36 kHz to produce tilting frequencies of 12.32 and 3.18 kHz for scanning. A Lissajous scan pattern was created with 300×300 pixels at 20 frames per sec, or 400×400 pixels at 10 frames per sec, to cover a FOV of 250×250 µm². The pixel spacing was 0.83 µm, and at 20 Hz frame rate we were under sampling a bit to maintain a higher frame rate to incur less motion artifact. Custom software, developed in LabView, was used to drive the MEMS scanner and reconstruct the image by remapping the time series signal in a 2D matrix.

Figure 4A:
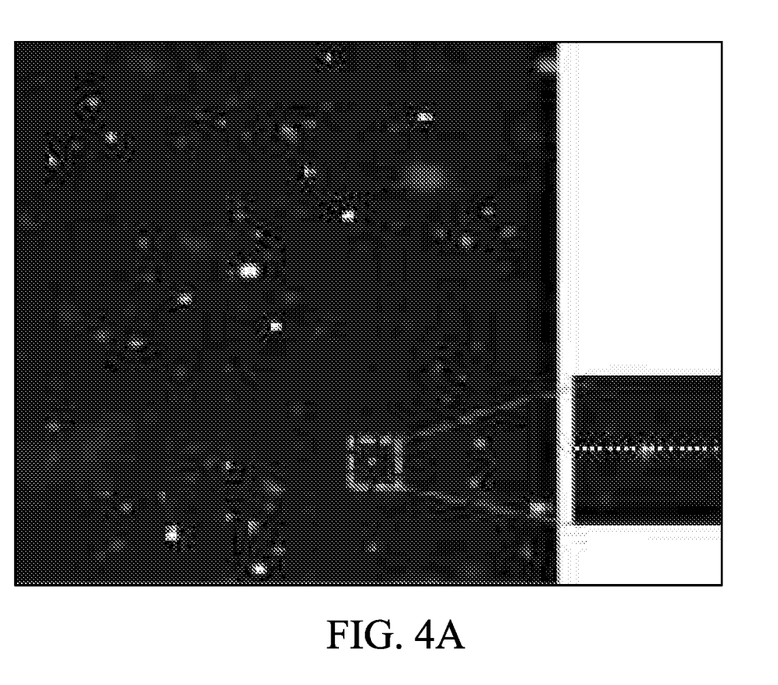
FIGS. 4A-4D illustrate a collected reflectance image of a 0.1 µm fluorescent bead (FIG. 4A), a plot of the intensity profile along the 0.1 µm fluorescent bead illustrating a lateral resolution defined by the full-width-at-half-maximum (FIG. 4B), a collected reflectance image of a standard resolution target (FIG. 4C), and a collected reflectance image of a lens paper showing individual fibers (FIG. 4D), respectively, in accordance with an example. The collected reflectance images are fluorescence images in these examples, collected with a signal-axis confocal endomicroscope, in accordance with an example.
Figure 4B:
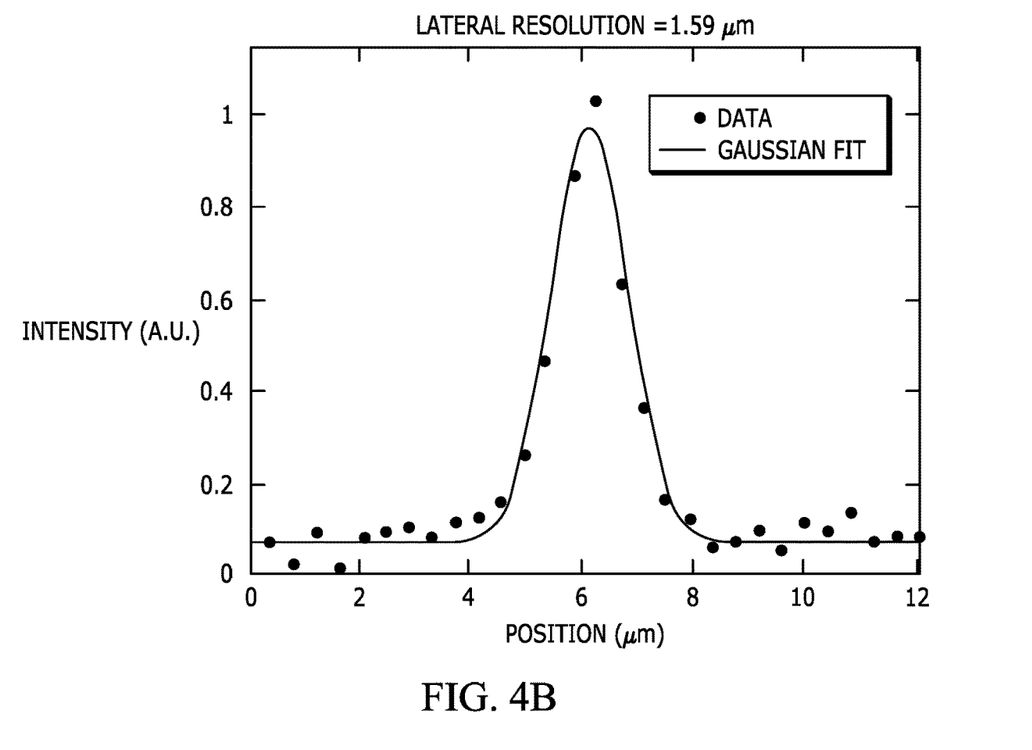
Figure 4C:
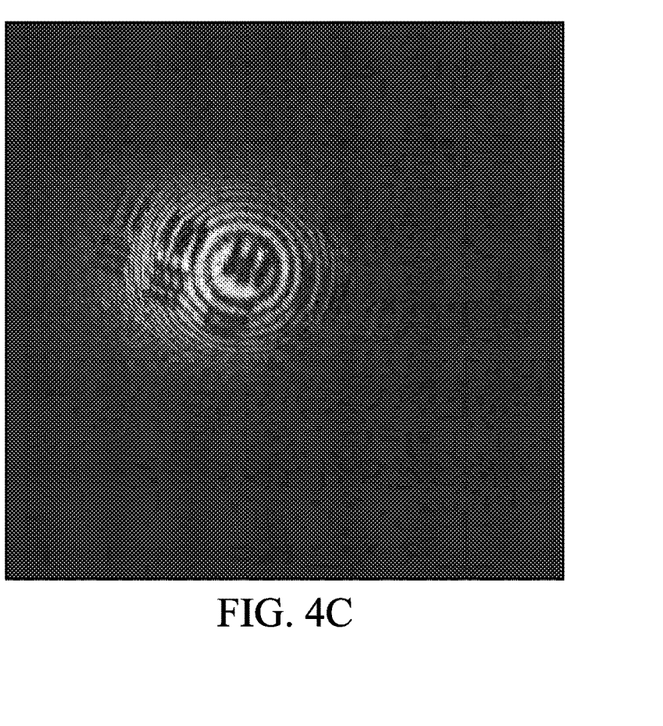
Figure 4D:
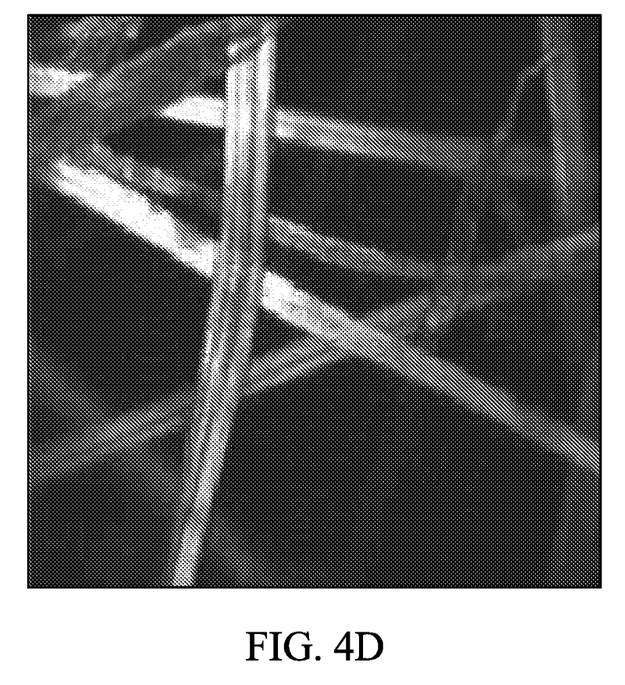

In FIG. 4B, we plot the intensity profile along a 0.1 µm fluorescent bead (FIG. 4A) to measure a lateral resolution of 1.59 µm, defined by the full-width-at-half-maximum (FWHM) of the intensity profile. Also, as shown, we collected reflectance images from a standard resolution target to qualitatively estimate a lateral resolution <2 µm (group 7, element 6 in expanded view of box), FIG. 4C. Fluorescence image of a lens paper shows individual fibers could be visualized by the endomicroscope, FIG. 4D.

Figure 5A:
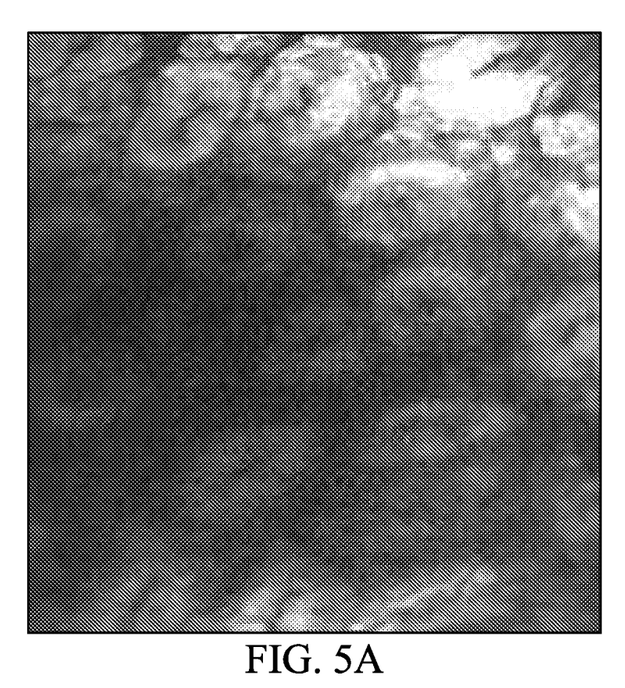
FIG. 5A is a fluorescence image collected ex vivo from mouse colon using a single-axis confocal endomicroscope, in accordance with an example herein.
Figure 5B:
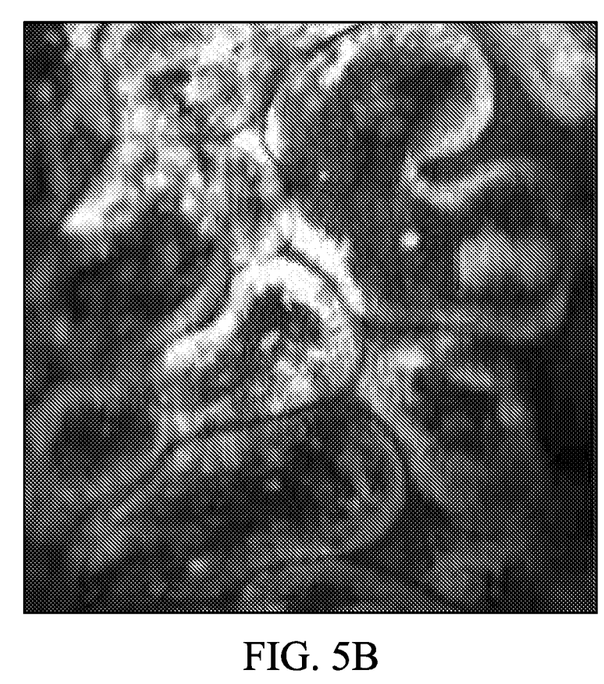
FIG. 5B is a fluorescence image collected ex vivo from mouse kidney.
Figure 5C:
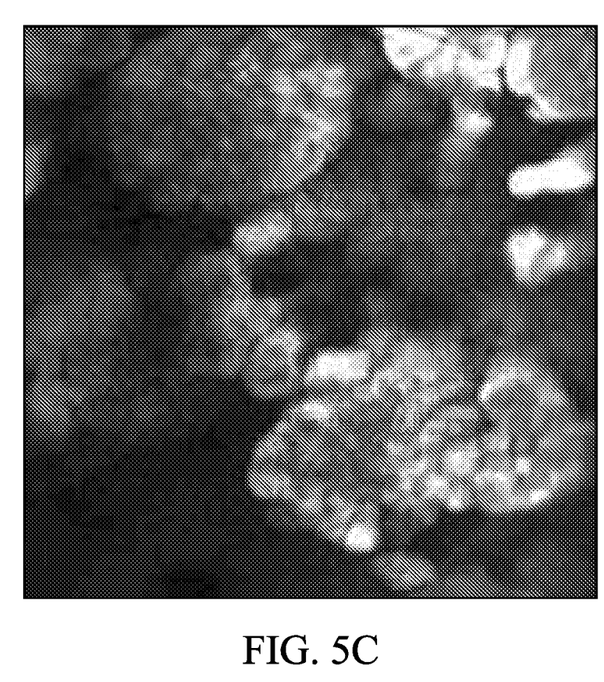
FIG. 5C is a fluorescence image collected ex vivo from mouse stomach.

FIG. 5A illustrates a fluorescent image of ex vivo analysis of a mouse colon. We performed an intravenous injection of 10% fluorescein sodium in a volume of 10 µL to a 10-week old mouse. After injection, the mouse was euthanized and excised colon tissue was imaged under the endomicroscope of the present designs, as shown in FIG. 5A. Representative image data from the mouse is shown for comparison in FIG. 5B (Kidney) and FIG. 5C (stomach).

Figure 6:
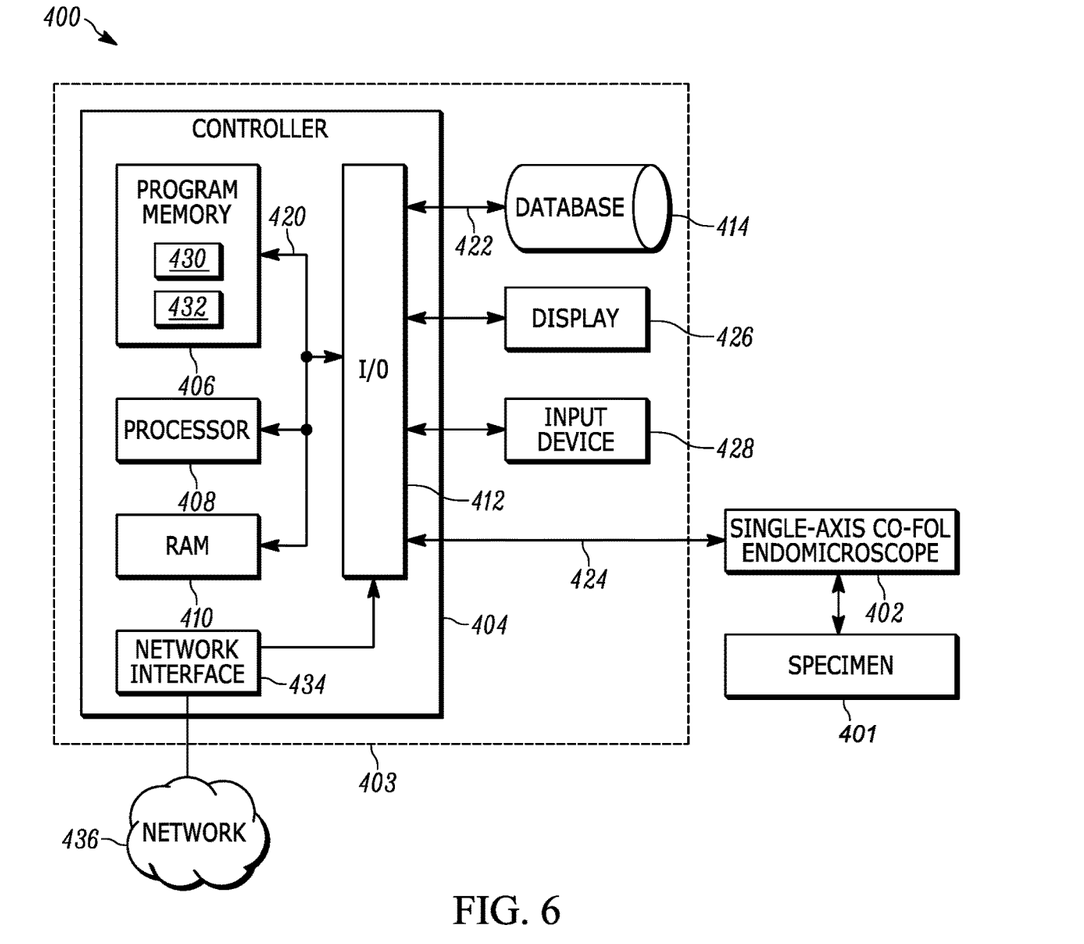
FIG. 6 is an block diagram of an example single-axis endomicroscope imaging system, in accordance with an example.

FIG. 6 is an example block diagram 400 illustrating the various components used in implementing an example embodiment of a single-axis confocal endomicroscope system. The single-axis confocal endomicroscope 402 may be positioned adjacent or operatively coupled to a specimen 401. The control device 403 may have a controller 404 operatively connected to a database 414 via a link 422 connected to an input/output (I/O) circuit 412. While not shown, additional databases may be linked to the controller 404 in a known manner. The controller 404 includes a program memory 406, a processor 408 (which may be a microcontroller or a microprocessor), a random-access memory (RAM) 410, and the input/output (I/O) circuit 412, all of which are interconnected via an address/data bus 420. Although only one microprocessor 408 is shown, the controller 404 may include multiple microprocessors 408. Similarly, the memory of the controller 404 may include multiple RAMs 410 and multiple program memories 406. Although the I/O circuit 412 is shown as a single block, it should be appreciated that the I/O circuit 412 may include a number of different types of I/O circuits. The RAM(s) 410 and the program memories 406 may be implemented as semiconductor memories, magnetically readable memories, and/or optically readable memories, for example. A link 424 may operatively connect the controller 404 to endomicroscope 402 through the I/O circuit 412.

The program memory 406 and/or the RAM 410 may store various applications (i.e., machine readable instructions) for execution by the microprocessor 408. For example, an operating system 430 may generally control the operation of the endomicroscope 402 and provide a user interface to the testing apparatus to implement the processes described herein. The program memory 406 and/or the RAM 410 may also store a variety of executive instructions 432 for accessing specific functions of the endomicroscope 402. By way of example, and without limitation, the executive instructions 432 may include, among other things: instructions for controlling operation of the endomicroscope 402, or other endoscopic devices, as described herein; instructions for capturing images with the endomicroscope 402 as described herein; and other instructions, for example, implementing software keyboard functionality, interfacing with other hardware in the endomicroscope 402, etc. The program memory 406 and/or the RAM 410 may further store data related to the configuration and/or operation of the endomicroscope 402, and/or related to the operation of one or more instructions. For example, the data may be data gathered by the endomicroscope 402, data determined and/or calculated by the processor 408, etc. In addition to the controller 404, the endomicroscope 402 may include other hardware resources. The endomicroscope 402 may also be coupled to various types of input/output hardware such as a visual display 426 and input device(s) 428 (e.g., keypad, keyboard, etc.) to fine tune actuation of the lateral scanning. In an embodiment, the display 426 is touch-sensitive, and may cooperate with a software keyboard routine as one of the software routines 432 to accept user input.

The present techniques provide an ultra-compact single-axis confocal endomicroscope design. With the present techniques, a 2.4 mm diameter microsystems-based confocal laser endomicroscopy capable of passing easily through the 2.8 mm biopsy channel of a standard medical endoscope can be achieved. The optical design uses a folded path to expand the beam and achieve NA=0.41 for diffraction-limited resolution on-axis. The resulting endomicroscopes can be used at the point-of-care to avoid the long processing times required by physical biopsies and provide physicians with instant pathology feedback during the procedure.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An endomicroscope assembly comprising:
a fiber ferrule and a single-mode optical fiber extending into the fiber ferrule, the fiber ferrule having a distal end positioned to emit an illumination beam when provided to the single-mode optical fiber;
a compact scanning assembly mounted to the flexible tubing, the compact scanning assembly having a folded beam configuration to receive the illumination beam, to convert the illumination beam to a higher numerical aperture illumination beam, and to scan the higher numerical aperture illumination beam across a lateral sample region, the compact scanning assembly comprising:
an outer housing;
a dual mirror lateral scanning assembly fixedly positioned within the outer housing and adjacent the distal end of the flexible tubing, the dual mirror lateral scanning assembly having a first scanning mirror with an aperture aligned with the single mode fiber to receive the illumination beam into a folded beam path for converting to the higher numerical aperture illumination beam, the folded beam path being defined by the first scanning mirror and a second mirror; and
a lens assembly fixedly positioned within the rigid outer housing, the lens assembly positioned distally to the lateral scanning assembly to scan the higher numerical aperture illumination beam across the lateral sample region and to collect fluorescence from the lateral sample region, wherein the dual mirror lateral scanning assembly and the lens assembly are axially aligned with the axis of the single-mode optical fiber.

2. The endomicroscope assembly of claim 1, wherein the outer housing of the compact scanning assembly has an outer diameter of 2.4 mm.

3. The endomicroscope assembly of claim 1, wherein the outer housing of the compact scanning assembly has an outer diameter of below 2.4 mm.

4. The endomicroscope assembly of claim 1, wherein the lens assembly comprises a plurality of lens elements.

5. The endomicroscope assembly of claim 4, wherein the plurality of lens elements comprises two achromatic doublet lenses.

6. The endomicroscope assembly of claim 5, wherein the plurality of lens elements comprises a plano-convex lens.

7. The endomicroscope assembly of claim 1, wherein the second mirror is an axial scanning mirror.

* * * * *